United States Patent [19]

Weisman

[11] Patent Number: 5,176,664
[45] Date of Patent: Jan. 5, 1993

[54] FEMALE VOIDING ASSIST DEVICE AND METHOD

[76] Inventor: Kenneth Weisman, 9 Tanglewood Cir., Rose Valley, Pa. 19065

[21] Appl. No.: 594,762

[22] Filed: Oct. 9, 1990

[51] Int. Cl.$^5$ .............................................. A61M 25/00
[52] U.S. Cl. .................... 604/317; 604/323; 604/329; 604/280; 128/761
[58] Field of Search ...................... 604/8–10, 604/317, 323, 327–331, 280, 282; 128/761

[56] References Cited

U.S. PATENT DOCUMENTS

| | | | |
|---|---|---|---|
| 4,416,657 | 11/1983 | Berglund | 604/9 |
| 4,474,569 | 10/1984 | Newkirk | 604/8 |
| 4,690,677 | 9/1987 | Erb | 604/329 |
| 4,846,818 | 7/1989 | Keldahl et al. | 604/330 X |
| 4,875,898 | 10/1984 | Eakin | 604/331 |
| 4,913,683 | 4/1990 | Gregory | 604/8 |
| 5,052,998 | 10/1991 | Zimmon | 604/8 |

Primary Examiner—Robert A. Hafer
Assistant Examiner—Kerry Owens
Attorney, Agent, or Firm—Caesar, Rivise, Bernstein, Cohen & Pokotilow, Ltd.

[57] ABSTRACT

A female voiding assist device for partial insertion in the bladder of a person. The device is a flexible catheter having a proximal end and a distal end and openings along the length thereof. The proximal end is set in a curl and is adapted to be inserted within the bladder. At least a portion of said device is positioned within the urethra of a person. An actuation device extends from a point adjacent the distal end to a point adjacent the sphincter whereby the actuation device is urged outwardly of the sphincter to permit voiding the bladder.

The method of facilitating female voiding involves inserting within a female person the aforesaid catheter.

5 Claims, 1 Drawing Sheet

FEMALE VOIDING ASSIST DEVICE AND METHOD

BACKGROUND OF THE INVENTION

This invention relates to a female voiding assist device and method and particularly relates to a novel urethral device to enable female voiding where natural urination does not occur.

There is a class of ureteral catheters or drainage tubes to assure the passage of urine from the kidneys to the bladder. Examples of such devices are shown in U.S. Pat. Nos. 4,531,933; 4,643,716 and 4,671,795.

There also has been a suggestion of a urethral catheter in U.S. Pat. No. 4,784,651, the purpose of which was to open and keep open the urethra and thereby permit the flow of urine from the bladder to and through the sphincter.

BRIEF SUMMARY OF INVENTION

The present invention is believed to be a marked improvement over the urethral device of U.S. Pat. No. 4,784,651. The present invention is useful in women who for physiological or other reasons, do not have the necessary muscle control to permit the urine to flow from the bladder through the urethra and then to and beyond the sphincter.

The present invention provides a rigid plastic stent that is initially positioned within a flexible plastic catheter having openings along the length thereof. The rigid stent is useful in the insertion process whereby the flexible plastic catheter is at least partially or wholly inserted within the bladder.

The catheter has a proximal end which is set is the form of a curl. The catheter also has an intermediate portion and a distal end. In use, at least the proximal end is inserted within the bladder, with the distal end of the catheter being at least partially located within the urethra. An actuation device, such as a string with a pull tab extends from the distal end and projects outwardly of the body, just beyond the sphincter. Finally, there is a bump or enlarged portion located on the distal end of the catheter to enable the user to know when the distal end has been sufficiently withdrawn such that urine flow will occur.

From the foregoing, it can be seen that an object of the present invention is to provide a female voiding assist device and method of insertion and use which can bring relief to women who have difficulty in urination.

Another object of the present invention is to provide a device which will either prevent closing of the urethra or establish a sufficient passageway in the urethra or through the device itself to permit the drainage of urine from the bladder.

DETAILED DESCRIPTION OF THE INVENTION

Figure 2:
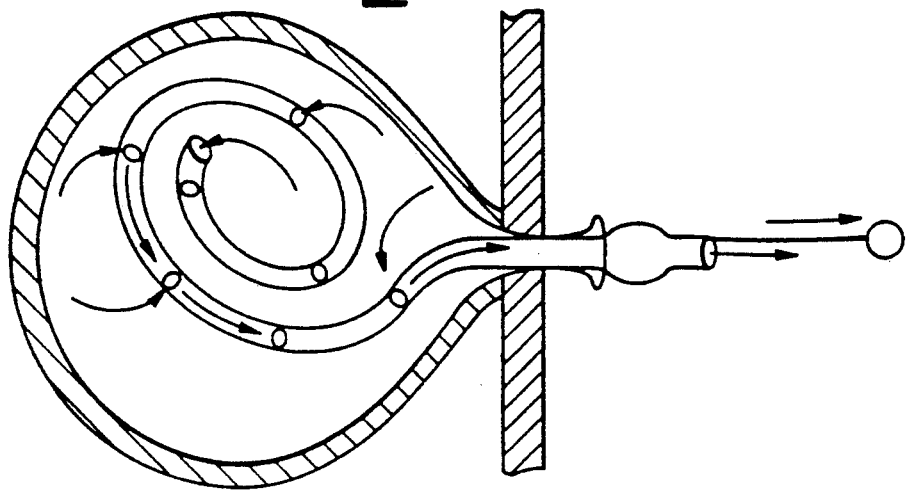
FIG. 2 is a view similar to FIG. 1, but wherein the actuation device has been utilized to bring the distal end outwardly of the sphincter and thereby permit urine flow.

Referring now in greater detail to the various figures of the drawing, wherein like reference characters refer to like parts, it will be seen that the invention has two aspects.

First, the invention is for a combination rigid plastic stent 10 initially positioned within a flexible plastic catheter 12 and having apertures along the length thereof. The catheter 12 as positioned on rod 10 is inserted within the urethra of a woman for permitting voiding to take place. The invention is also for a method of use of the rod-catheter device.

The apertures 14 in the catheter 12 are for drainage and circulation. Should a clot form within the catheter after insertion in the urethra, drainage from the urethra can occur by having the draining fluid exit from one of the apertures 14 and travel along the outside of the catheter. Such fluid may then continue to drain along the outside of the catheter or can reenter the tube through another opening.

The catheter 12 has proximal end 18 which is set in the form of a curl. The catheter also has an intermediate portion 20 and a distal end 22 to which is attached a pulling or actuation device 24 such as a string with pull tab 26. There is also a bump 28 or enlarged portion located on the distal end 22.

In the preferred embodiment, the proximal end 18 is sealed and the distal end 22 is open, although catheter 12 can be manufactured such that the distal end 22 is also sealed, with such sealed end being opened prior to or during surgery.

The catheter 12 is made of an inert material, such as a silicone plastic as has been used in prior urethral devices, such as disclosed in U.S. Pat. No. 4,784,651, the entire disclosure of which is incorporated herein by reference. Other materials as disclosed in U.S. Pat. No. 4,784,651 are usable in the invention. The overall length of the catheter 12 is at least 20 centimeters and its calibre (outside diameter) is in the range of 14 french.

The calibre (outside diameter) of the catheter 12 should be substantially uniform and the lumen (inside diameter) of tube 12 should also be substantially constant throughout.

The proximal end 18 of catheter 12 is approximately 15 centimeters in length. The proximal end will revert to its curled shape (memory) after insertion into the bladder.

The distal end 22 of catheter 12 is approximately 5 centimeters in length beyond bump 28, and can be shortened by removing a portion of the end to tailor the overall length of the device to the needs of any specific patient.

Figure 1:
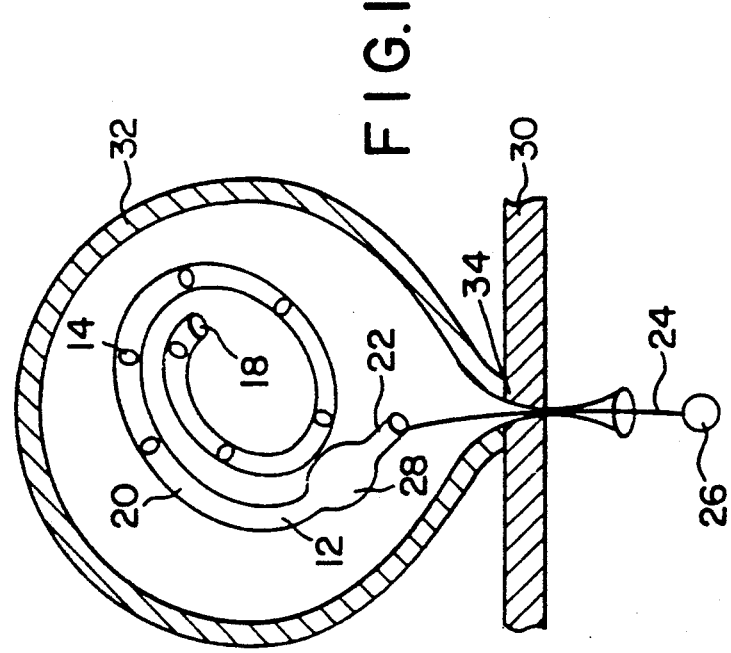
FIG. 1 of the sectional view showing the female voiding assist device of the present invention inserted within the bladder, with the actuation device or pull extending outwardly of the sphincter.

As shown in FIG. 1, the catheter is shown in its normal inserted position within the bladder 32. Voiding or draining of the bladder cannot occur because distal end is still located within the bladder. FIG. 2 shows the catheter 12 having brought to the extended position by urging of the chain 26 outwardly of the sphincter 30 so that the distal end 22 of the catheter 12 is positioned outside of the of the urethra as shown in FIG. 2. When voiding, the distal end 22 is slightly extended beyond the urethra and outwardly of the sphincter. However, the curled proximal 18 end at all times remains in the bladder as shown in FIG. 2.

In such extended position (FIG. 2), the urine in the bladder can now drain or pass by gravity into one or more of the openings of the catheter 12 and then downwardly through the catheter 12 to be discharged.

Figure 3:
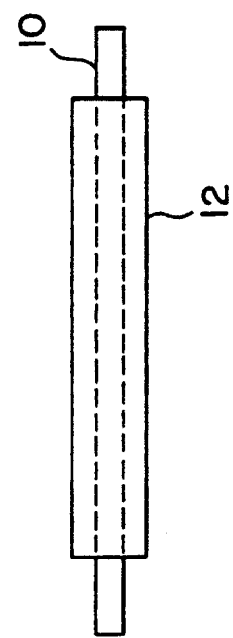
FIG. 3 is a view showing the rigid plastic stent initially positioned within the flexible plastic catheter, prior to insertion of the catheter within the bladder.

The catheter 12 is utilized in the following fashion. The plastic 12 french stent 10 is inserted through the urethra 34 and into the bladder 32. The catheter 12 is then placed over the stent as shown in FIG. 3 and slid up into the bladder 32 over the plastic stent or rod 10. The pulling string remains hanging from the urethra with a small button or tab 26 so that the device may be activated when needed. Once the stent or rod 10 is withdrawn, the curl at the proximal end 18 reforms to prevent migration of the device out of the bladder. Also, the lower portion or distal end 22 of the rod 10 is seated in the bladder 32 and no egress of urine from the bladder occurs.

Once the stent 10 is withdrawn, the curl at the proximal end 18 reforms as shown in FIG. 1 to prevent migration of the catheter 12 out of the bladder 32. Also, the lower portion of the catheter 12 is seated in the bladder such that it prevents egress of urine from the bladder.

The catheter 12 is produced from a flexural and resilient material which is clinically acceptable and sufficiently durable in use. It is preferably in the vicinity of 0.2 mm thick. Examples of materials from which the tube may be formed are silicone, urethane or polyvinyl chloride.

A collapsible-walled device having these properties will permit substantially normal, or any remaining sphincter muscle operation in patients suffering from incontinency. This will simulate normal physiological functions as far as possible.

From the foregoing, it can be seen that the invention has two aspects. First, a plastic relatively rigid, hollow stent 10 of preferably 12 french outer diameter having no apertures along the length thereof but having a slightly tapered leading edge. Second, a slightly larger catheter device (tube 12) of approximately 14 french, having apertures along its length, except possibly for the most distal segment. As seen in FIG. 3, stent 10 is initially positioned within the catheter 12.

The apertures in the catheter 12 are for drainage and circulation. Should a clot form in the catheter, drainage can continue to occur by having the draining fluid exit from one of the apertures and travel along the outside of the catheter. Such fluid may then drain along the outside of the catheter or it can re-enter the tube through another opening 12.

The catheter preferably has an inside diameter of 14 French and is made of a soft plastic substance with memory. The proximal end 18 curls if not straightened by the plastic stent 10. There is also an intermediate portion 20 and a distal end 22 to which is attached a pulling device (string). Approximately 3 cm. before the end of the catheter is a bump 28 or an enlarged portion of the catheter. In a modified embodiment, both ends of the plastic catheter 12 are open.

The 12 french plastic stent or rod 10 is made of rigid inert material such as rigid vinyl plastic. The overall length of rod 10 is approximately 20 cm. The outside of the rod 10 is uniform as is the lumen throughout its length.

The catheter 12 is slightly shorter than the stent as shown in FIG. 3. The proximal end 18 of the catheter 12 will revert to its curled shape after insertion to the bladder with removal of the stent. The distal end 22 is approximately 5 cm in length and can be shortened by removing a portion of the distal end from the overall length of the catheter to the needs of a specific patient.

The catheter 12 in FIG. 1 is shown in its normal inserted position within the bladder 32. Urination or drainage of the bladder cannot occur because of normal sphincter tone. FIG. 2 shows the catheter 12 having been brought through the urethra 34 by pulling on the string outwardly so that the distal end 22 of the catheter 12 is positioned beyond the urethra as shown in FIG. 2. The person can grasp the bump 28 in order to know that the distal end has been sufficiently withdrawn so that voiding can occur. When voiding, the distal end 22 can pass so that it is slightly out of the urethra and extends beyond the body or sphincter. The curled proximal portion 18 remains within the bladder 32 at all times, except upon the device's removal.

In the extended position of FIG. 2, urine in the bladder can now drain or pass by gravity through one or more of the openings in the catheter 12 and then downwardly through the device to be discharged.

Without further elaboration, the foregoing will so fully illustrate my invention that others may, by applying future knowledge, adopt the same for use under various conditions of service.

What I claim as the invention is:

1. A urine collection system for a female person for insertion in part of the bladder of such person, said system comprising a flexible catheter having a proximal portion, an intermediate portion and a distal portion having indicating means adjacent the end thereof, said catheter also having openings along the length thereof, at least the proximal portion being set in a curl and being inserted within the bladder, at least a portion of said intermediate portion being positioned within the urethra of a person when in use, and actuation means for urging said distal portion outwardly through said urethra, said actuation means extending outwardly when not in use from said distal portion to a point adjacent the sphincter, said actuation means being positioned outwardly of the sphincter when said actuating means in pulled, and whereby said proximal portion will at least partially uncurl as said intermediate portion moves within said urethra, and said distal portion is urged sufficiently outwardly to be withdrawn to permit and achieve voiding of the bladder with said indicating means indicating to the user when said distal portion has been sufficiently withdrawn, and wherein urine flows through said urethra to be discharged beyond said urethra, and said distal portion is then permitted under release of said actuating means to return to its original position under a retracting force exerted as said proximal portion recurls to its original position.

2. The invention of claim 1 wherein said system is made of flexible plastic.

3. The invention of claim 1 including a rigid stent initially positioned within said catheter to facilitate insertion within a person.

4. The method of facilitating female voiding comprising inserting within a female person the catheter of claim 1.

5. The invention of claim 1 wherein said indicating means is a bump.